US012673125B2

(12) United States Patent
   Karitonas

(10) Patent No.:  US 12,673,125 B2
(45) Date of Patent:       Jul. 7, 2026

(54) UV EMITTER AND CONTROLLER FOR DISINFECTION OF SPACES

(71) Applicant: Specialist Health Solutions Limited, Kings Lynn (GB)

(72) Inventor: Tautvydas Karitonas, Kings Lynn (GB)

(73) Assignee: Specialist Health Solutions Limited (GB)

( * ) Notice:   Subject to any disclaimer, the term of this patent is extended or adjusted under 35 U.S.C. 154(b) by 1156 days.

(21) Appl. No.: 17/366,841

(22) Filed:   Jul. 2, 2021

(65)        Prior Publication Data
      US 2022/0008589 A1      Jan. 13, 2022

(30)        Foreign Application Priority Data
      Jul. 9, 2020   (GB) ..................................... 2010591

(51) Int. Cl.
   A61L 2/24       (2006.01)
   A61L 2/10       (2026.01)
            (Continued)
(52) U.S. Cl.
   CPC .................. A61L 2/24 (2013.01); A61L 2/10 (2013.01); A61L 2/26 (2013.01); *A61L 2103/75* (2026.01);
            (Continued)
(58) Field of Classification Search
   CPC ..... A61L 2/10; A61L 2/24; A61L 2/26; A61L 2202/11; A61L 2202/14; A61L 2202/25; A61L 2/28; A61L 9/20
   See application file for complete search history.

(56)        References Cited

U.S. PATENT DOCUMENTS 6,592,816 B1 *   7/2003   Ebel .......................... A61L 2/10
                                                                          422/62
10,556,025 B2   2/2020   Ufkes
            (Continued)

FOREIGN PATENT DOCUMENTS

GB        2531151 A      4/2016

OTHER PUBLICATIONS

European Search Report dated Dec. 2, 2021 issued in corresponding Patent Application No. 21181600.4 (7 pages).

*Primary Examiner* — Brendan A Hensel
(74) *Attorney, Agent, or Firm* — Barnes & Thornburg; Anusuya Das

(57)        ABSTRACT

The invention is directed to disinfection of object(s) in a space using a UV emitter. A calibration process is performed in which one or more UV sensors are placed proximate the object or set of objects to be disinfected. The sensor(s) measure a UV dose and the time taken for the UV dose to equal to a level suitable for disinfection to occur to the required level is measured. This is saved in a database in association with an identification of the object(s) being disinfected. This saved program can be activated subsequently and without the sensors present to disinfect the object(s). In addition to the calibration process, or in the alternative, the controller may enable the operator to select a particular pathogenic organism or set of organisms as a target of the disinfection process, with the controller accessing the database to obtain a disinfection program specific to the target.

7 Claims, 5 Drawing Sheets

(51) Int. Cl.
  *A61L 2/26*    (2006.01)
  *A61L 103/75*   (2026.01)
(52) U.S. Cl.
  CPC ........ *A61L 2202/11* (2013.01); *A61L 2202/14*
                 (2013.01)

(56)      References Cited

U.S. PATENT DOCUMENTS

| | | | |
|---|---|---|---|
| 2012/0305787 A1* | 12/2012 | Henson | A61L 2/10 |
| | | | 250/492.1 |
| 2013/0175460 A1* | 7/2013 | Farren | A23L 3/28 |
| | | | 250/504 R |
| 2013/0330235 A1 | 12/2013 | Stibich et al. | |
| 2014/0044590 A1 | 2/2014 | Trapani | |
| 2014/0212332 A1* | 7/2014 | Bergman | G01J 1/429 |
| | | | 422/24 |
| 2014/0341777 A1 | 11/2014 | Deshays et al. | |
| 2015/0209457 A1 | 7/2015 | Bonutti et al. | |
| 2016/0235879 A1* | 8/2016 | Andersson | G06F 21/31 |
| 2016/0354503 A1 | 12/2016 | Hutchens et al. | |
| 2019/0091738 A1* | 3/2019 | Chen | B60H 1/00742 |
| 2019/0298869 A1 | 10/2019 | Poulsen | |
| 2020/0179543 A1 | 6/2020 | Deshays et al. | |
| 2021/0369905 A1* | 12/2021 | Bosua | F21V 23/045 |

* cited by examiner

Fig. 2

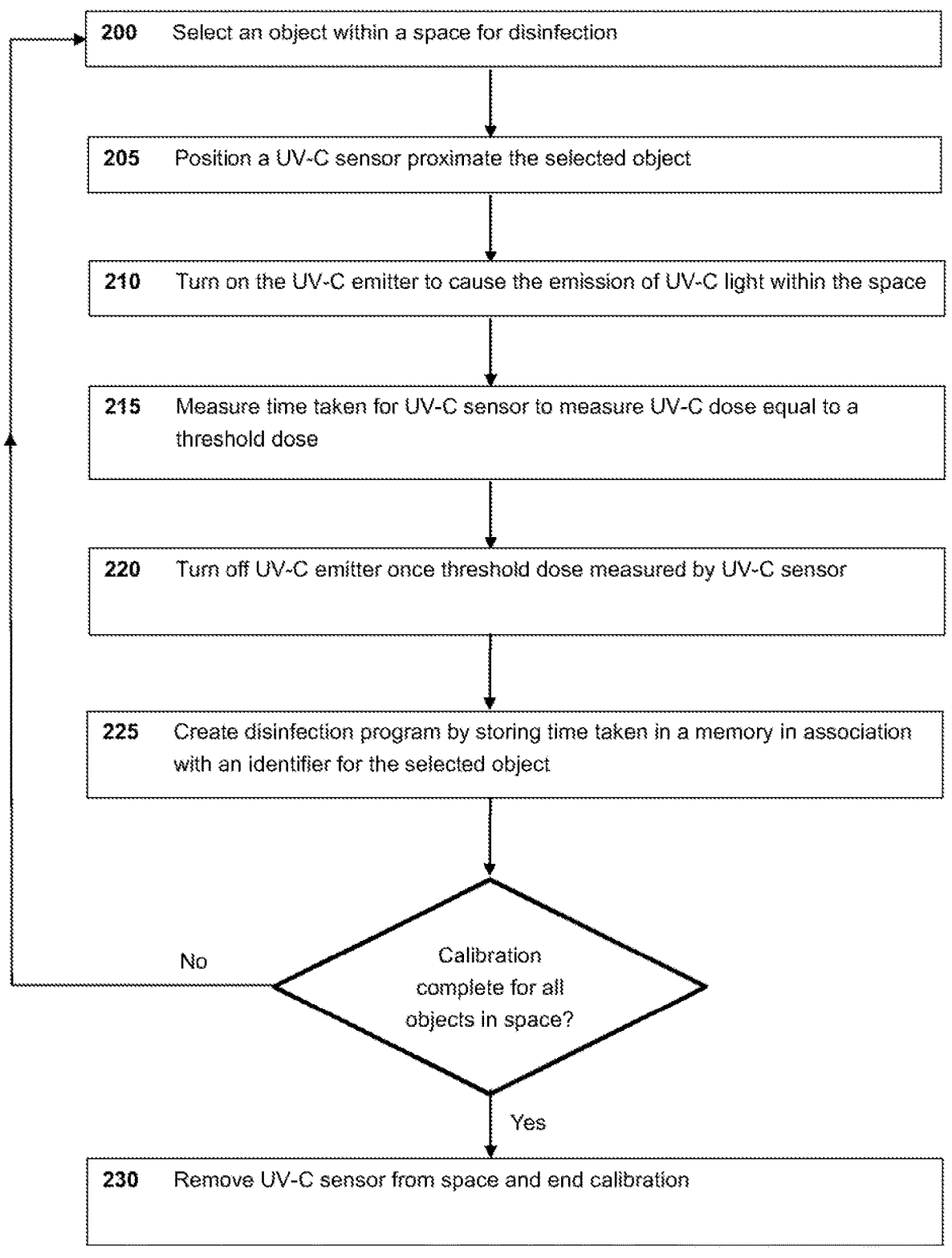

200    Select an object within a space for disinfection

205    Position a UV-C sensor proximate the selected object

210    Turn on the UV-C emitter to cause the emission of UV-C light within the space 215    Measure time taken for UV-C sensor to measure UV-C dose equal to a threshold dose 220    Turn off UV-C emitter once threshold dose measured by UV-C sensor 225    Create disinfection program by storing time taken in a memory in association with an identifier for the selected object No          Calibration complete for all objects in space?

Yes

230    Remove UV-C sensor from space and end calibration

| 300 | Access a set of stored disinfection programs using a user interface of controller |

| 305 | Select a disinfection program corresponding to the object that is to be disinfected |

| 310 | Turn on UV-C emitter 110 for an amount of time specified by the selected disinfection program |

Fig. 5

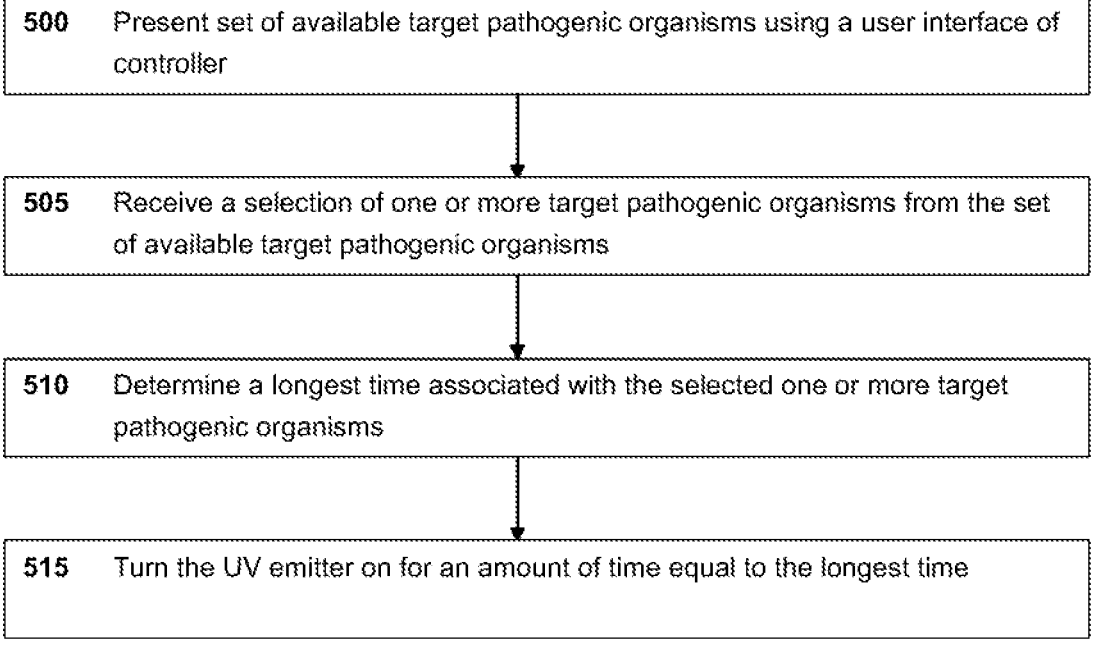

| 500 | Present set of available target pathogenic organisms using a user interface of controller |

| 505 | Receive a selection of one or more target pathogenic organisms from the set of available target pathogenic organisms |

| 510 | Determine a longest time associated with the selected one or more target pathogenic organisms |

| 515 | Turn the UV emitter on for an amount of time equal to the longest time |

UV EMITTER AND CONTROLLER FOR DISINFECTION OF SPACES

CROSS-REFERENCE TO RELATED APPLICATIONS

This application claims priority of Great Britain Application No. 2010591.2, filed on Jul. 9, 2020, entitled "UV EMITTER AND CONTROLLER FOR DISINFECTION OF SPACES", the contents of which is expressly incorporated herein by reference in its entirety.

FIELD OF INVENTION

This invention relates generally to the disinfection of spaces, and particularly to the disinfection of specific objects within a space using UV light. Specific pathogenic organisms may also be targeted.

BACKGROUND

There are many circumstances in which it is desirable to be able to disable or kill pathogens in a space. One technique for doing so is the irradiation of air and/or surfaces in the space with ultraviolet light in the UV band, which is usually defined in the context of pathogen eradication as electromagnetic radiation with a wavelength in the range of 100-420 nm (i.e. encompassing the UV-A, UV-B and UV-C bands). Sometimes a particular focus is placed on the UV-C band, which is usually defined as electromagnetic radiation with a wavelength in the 100-280 nm range, perhaps with a specific focus on radiation with wavelength 200-280 nm.

A key consideration with such systems is their efficacy. It is important that surfaces being disinfected receive a sufficient dose of UV light to disable or kill a very high proportion of pathogens on the surface, e.g. 99.99%, 99.999% or even 99.9999% of pathogens. Failure to achieve this high disable or kill percentage can leave surfaces with sufficient quantities of live pathogens to cause infection.

In a typical space objects will be present that block UV light, casting shadows in which pathogens may receive a lower than expected dose of UV light and therefore unexpectedly survive a disinfection cycle. For this reason the rated UV light output of a UV light emitter (e.g. a UV emitting bulb) is not usually a reliable measure of disinfection efficacy.

One solution to this problem is to expose a space to far more UV light than is required to disable or kill pathogens, i.e. to leave the UV emitter on for a long time. This is typically effective in reliably achieving a desired disable/kill rate but is not a perfect solution. This is because it exposes some surfaces in the space to a greater intensity of UV light than is strictly necessary to achieve the required disinfection efficacy. This can cause damage to these surfaces, particularly if they contain materials that degrade under UV light such as plastics. This is further exacerbated in scenarios where a space needs to be repeatedly disinfected relatively regularly, e.g. a room in a hospital or an emergency services vehicle such as an ambulance.

Another problem with this solution is that the space often cannot be used for its intended purpose whilst the decontamination cycle is taking place. This is because at least some wavelengths in the UV band are damaging to human tissues, meaning that a space must be secured to prevent people from entering it whilst disinfection using UV light is taking place. The longer the disinfection process, the longer the space is out of action, which is undesirable in many environments including hospitals and emergency services vehicles where a quick decontamination cycle that enables the space to be returned to its intended use quickly is clearly desirable.

Another solution to the above problem is to place UV sensors in the space before initiating the disinfection process. The sensors measure the intensity of UV light and can therefore take account of local discrepancies caused by shadows. This technique can be effective in avoiding unnecessary long disinfection cycles whilst maintaining disinfection efficacy but comes at the cost of the time and effort required to set up each sensor each time the disinfection process is initiated. Additionally, the complexity of the disinfection process is increased as it is necessary for operators to be trained in the placement and use of the sensors. Furthermore, in these types of system the sensors are often used to measure UV light that is reflected from surfaces in the space, rather than directly emitted UV light, which can give an inaccurate estimate of disinfection efficacy.

Another consideration is that in some circumstances it is only necessary to disinfect a particular object or set of objects in space, rather than the entire space. The time required to disinfect a particular object, e.g. a bed in a hospital room, may be less than the time required to disinfect the entire space. Existing systems do not provide the facility to selectively disinfect an object or set of objects in a space in a convenient and user-friendly manner, leading to unnecessarily long disinfection cycles which are undesirable for the reasons given above.

A further consideration is that the ability of a pathogenic organism to survive exposure to UV light typically varies from organism to organism. In order to achieve reliable kill/disable efficacy, existing disinfection systems assume a 'worst case' scenario and provide UV light for a time needed to kill/disable the hardiest of pathogenic organism. However, in practice the actual pathogenic organisms present on a surface may be far less resistant to UV light, leading to an unnecessarily long exposure of the space to UV light. This again results in the drawbacks outlined above in relation to more rapid degradation of materials such as plastic in the space and also downtime of the space.

SUMMARY OF THE INVENTION

Broadly speaking the invention is directed to a technique for disinfecting an object or set of objects in a space using a UV emitter that is located within the space. A calibration process is performed in which one or more UV sensors are placed proximate the object or set of objects to be disinfected. The sensor(s) measure a UV dose and the time taken for the UV dose to equal to a level suitable for disinfection to occur to the required level is measured. This time is saved in a database in association with an identifier that uniquely identifies the object(s) being disinfected, to define a disinfection program. This program can be activated subsequently using a controller and without the sensors present to initiate a disinfection cycle of the object(s). In addition to the calibration process, or in the alternative, the controller may enable the operator to select a particular pathogenic organism or set of organisms as a target of the disinfection process, with the controller accessing the database to obtain a disinfection program specific to the target.

In a first aspect the invention provides a method for configuring a disinfection apparatus, the disinfection apparatus secured to a fixed surface within a space and comprising a UV emitter, the method comprising: a) selecting a first object within the space for disinfection; b) positioning a first UV sensor proximate the first object; c) turning the UV emitter on to cause the emission of UV light within the space; d) measuring a time that is taken for the first UV sensor to detect a UV dose equal to a threshold dose; and e) creating a disinfection program by storing the time taken in a memory in association with an identifier for the first object.

In a second aspect the invention provides a method for disinfecting an object in a space using a disinfection apparatus secured to a fixed surface within the space and comprising a UV emitter, the method comprising: accessing a set of stored disinfection programs using a user interface of a controller communicatively coupled to the disinfection apparatus and located remotely from the disinfection apparatus; selecting a disinfection program from the set corresponding to the object, and turning the UV emitter on for an amount of time specified by the selected disinfection program.

In a third aspect the invention provides a method for disinfecting an object in a space using a disinfection apparatus secured to a fixed surface within the space and comprising a UV emitter, the method comprising: configuring the disinfection apparatus by: a) selecting a first object within the space for disinfection; b) arranging a first UV sensor proximate the first object; c) turning the UV emitter on to cause the emission of UV light within the space; d) measuring a time that is taken for the first UV sensor to measure a UV dose equal to a threshold dose; and e) creating a disinfection program by storing the time taken in a memory in association with an identifier for the first object; and initiating a decontamination cycle by: i) removing the UV sensor from the space; ii) selecting the disinfection program using a user interface of a controller coupled to the disinfection apparatus and to the memory; and iii) responsive to the selecting, automatically turning the UV emitter on for an amount of time specified by the disinfection program.

In a fourth aspect the invention provides a system for disinfecting a space, the system comprising: a UV emitter secured to a fixed surface within the space; a controller located remotely from the UV emitter; and a UV sensor; wherein the controller comprises a processor and a memory, the memory storing computer-readable instructions that, when executed, cause the processor to: transmit a control signal to the UV emitter to cause the UV emitter to turn on; determine a time taken for the UV sensor to measure a UV dose equal to a threshold dose; and create a disinfection program by storing the time taken in the memory in association with an identifier for a first object located proximate the UV sensor.

In a fifth aspect the invention provides a method for disinfecting a space using a disinfection apparatus comprising a UV emitter, the method comprising: presenting a set of available target pathogenic organisms using a user interface of a controller communicatively coupled to the disinfection apparatus and located remotely from the disinfection apparatus; receiving, by the controller, a selection of one or more target pathogenic organisms from the set of available target pathogenic organisms; determining, by the controller, a longest time associated with the selected one or more target pathogenic organisms; and turning the UV emitter on for an amount of time equal to the longest time.

In a sixth aspect the invention provides a system for disinfecting a space, the system comprising: a UV emitter; and a controller located remotely from the UV emitter; wherein the controller comprises a processor and a memory, the memory storing computer-readable instructions that, when executed, cause the processor to: present a set of available target pathogenic organisms using a user interface of the controller; receive a selection of one or more target pathogenic organisms from the set of available target pathogenic organisms; determine a longest time associated with the selected one or more target pathogenic organisms; and transmit a control instruction to cause the UV emitter to turn on for an amount of time equal to the longest time.

Further preferred features of the invention are set out in the appended dependent claims.

BRIEF DESCRIPTION OF THE DRAWINGS

FIG. 2 illustrates a method of configuring a disinfecting apparatus according to an embodiment of the invention.

FIG. 5 illustrates a method of performing a disinfection cycle targeting certain pathogenic organism(s) according to an embodiment of the invention.

DETAILED DESCRIPTION

Throughout this specification reference is made to UV band ultraviolet light. In the context of disinfection processes this typically refers to UV light in a wavelength range of 100-420 nm, i.e. the UV-A, UV-B and UV-C bands. A particular focus can be placed on the UV-C band (100-280 nm) and even a subpart of the UV-C band (200-280 nm) which is known to be particularly effective in elimination of some pathogens. It will be appreciated however that the present invention is in fact applicable to wavelengths outside of this range, providing that such wavelengths have disruptive effect to a target pathogen so as to have disinfection capabilities. Therefore, deviations from the wavelength range above, e.g. 90 nm, 80 nm, 430 nm, 440 nm, are also within the scope of the invention. Narrowband and broadband UV radiation sources are equally usable with the present invention.

In this specification reference is made to a UV dose. This is the product of UV light intensity as incident on a surface and the time for which the light is incident, typically expressed in units of millijoules per square centimetre (mJ/cm$^2$). Dose is therefore an appropriate unit for determining the total exposure of a surface to UV light.

References to a 'pathogenic organism' are understood to encompass any organism capable of causing disease in a host, including: bacteria, fungi, viruses, and the like.

Figure 1:
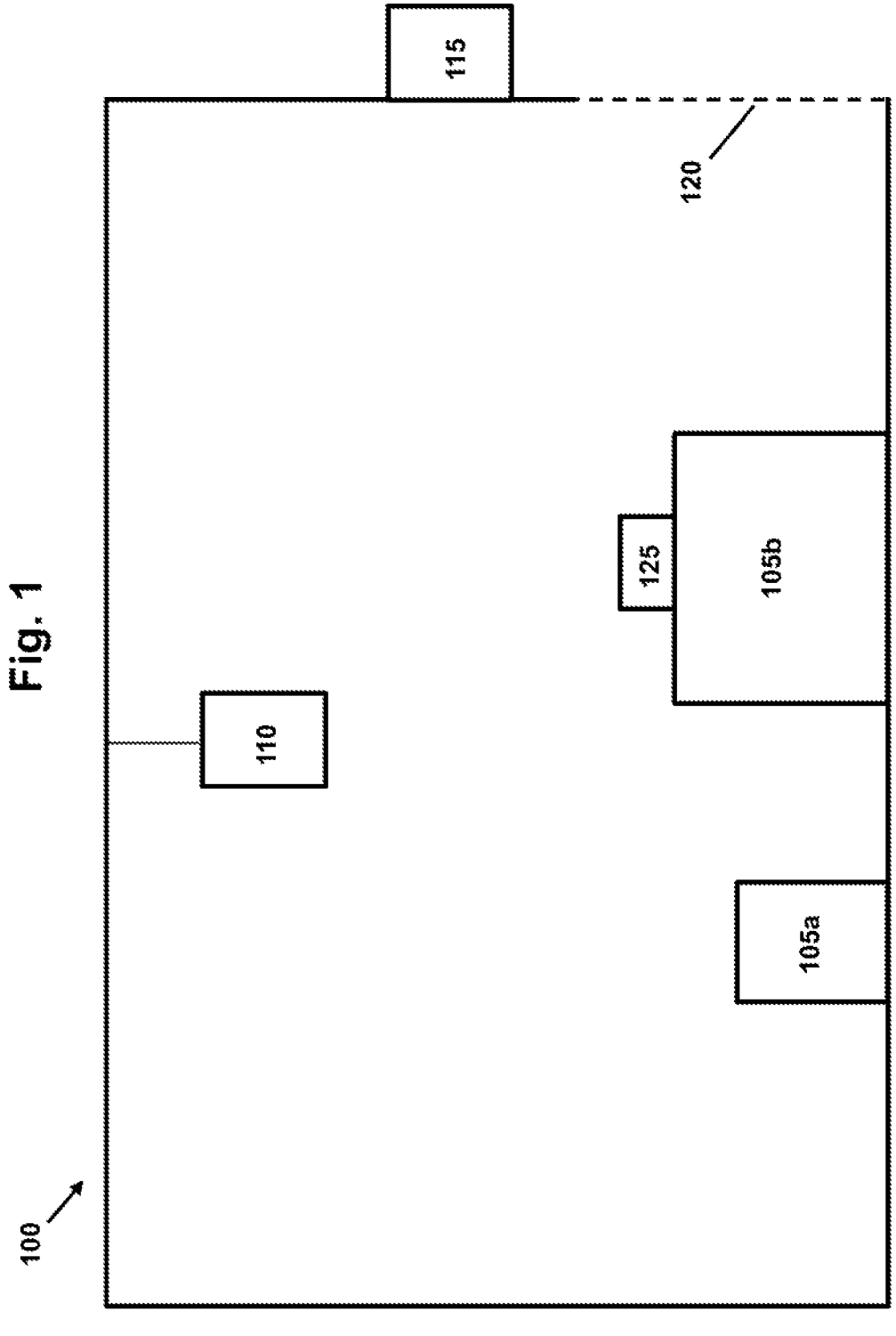
FIG. 1 is a schematic drawing of an arrangement suitable for implementing a calibration mode according to an embodiment of the invention.

FIG. 1 shows an arrangement suitable for implementing a calibration mode of the present invention. A space 100 containing objects 105a, 105b to be disinfected is shown in schematic form. Space 100 may be, for example, a room in a hospital, in which case objects 105a, 105b may be a chair and a bed. Space 100 could alternatively be a dentist's surgery, in which case objects 105a, 105b may be a chair and an instrument table. As a further alternative space 100 could be an interior of an emergency services vehicle such as an ambulance, in which case objects 105a, 105b could be an ambulance trolley and a medical supplies cabinet. This list is non-exhaustive and many variations are possible to both the space and the objects within it. It will also be appreciated that the invention is not limited to any particular number of objects and that the space may contain one or more objects for disinfection.

Space 100 also contains a disinfection apparatus comprising a UV emitter 110 that is fixed in location relative to space 100, e.g. by mounting emitter 110 to a fixed surface within space 100. That is, emitter 110 is not mobile. Equivalently, the distance between emitter 110 and fixed structures in space 100, e.g. walls, does not change with time. In the illustrated embodiment emitter 110 is mounted in a fixed arrangement to the ceiling of space 100, but this is not essential and emitter 110 could alternatively be mounted to a wall of space 100 or some other fixed structure within space 100, e.g. a support beam. The location of emitter 110 within space 100 will vary according to specifics of space 100 and is preferably chosen such that light produced by emitter 110 is able to reach the majority of space 100 without significant interruption. A skilled person having the benefit of the present disclosure will be able to determine a suitable location for emitter 110 in a given space without difficulty.

While only one emitter is shown in FIG. 1, it will be appreciated that the disinfection apparatus is not limited in this respect and that the disinfection apparatus can comprise more than one emitter fixedly mounted within space 100.

Emitter 110 itself comprises any suitable mechanism for generating UV light of a wavelength or set of wavelengths suitable for damaging and/or killing pathogens. For example, emitter 110 may include one or more germicidal UV lamps or tubes. The invention is not limited in this regard and any suitable UV generating mechanism is within its scope. Emitter 110 may be a narrowband emitter, a broadband emitter, or comprise multiple narrowband and/or broadband emitting components. Emitter 110 may emit specific wavelengths of UV light tuned to particular pathogens. Emitter 110 emit light falling within the UV-A, UV-B and/or UV-C wavelength band.

The disinfection apparatus may include a casing that is opaque to UV light. The casing may include a motor that enables the casing to be switched between an open and closed position. In the open position the casing allows UV light to pass from emitter 110 through openings and reach space 100, and in the closed position casing prevents substantially all UV light produced by emitter 110 from reaching space 100. In this way the casing can serve as a safety mechanism that can be engaged to prevent any person entering space 100 while emitter 110 is emitting UV light from being exposed to UV light.

The disinfection apparatus is communicatively coupled to controller 115 via a wired and/or wireless connection. Controller 115 includes a processor and a memory for storing digital data, as well as a human interface device that enables a person to submit commands and read off information. The human interface device may be, for example, a touchscreen, or a display and keyboard. The memory may be any form of computer-readable memory, e.g. RAM, ROM, etc. The memory may be physically located as part of controller 115 or it may be remotely located, e.g. a storage region in the Cloud. Controller 115 may include communications hardware such as a cellular radio and/or WiFi antenna, and the like, to enable the controller to communicate with a remote data processing device such as a Cloud-based server in order to access information including any information described herein as 'stored in the memory' of the controller.

Controller 115 is configured to send control signals to the disinfection apparatus for various purposes including adjusting the operation of emitter 110. Control signals include an ON command to cause emitter 110 to start producing UV light and an OFF command to cause emitter 110 to stop producing UV light. Controller 115 may also control other aspects of emitter 110, e.g. if the disinfection apparatus includes a casing, controller 115 may send control signals to cause the casing to open and close.

In the illustrated embodiment controller 115 is wall mounted and located outside of space 100 next to an entrance 120 to space 100. Entrance 120 is shown as a dashed line in FIG. 1 and in this exemplary case takes the form of a door. Controller 115 does not have to be wall mounted and alternatively can be mounted or otherwise located proximate space 100. As a further alternative controller 115 can be a portable device, e.g. a tablet computer, laptop computer, mobile telephone, and the like with a software application installed for communication with the disinfection apparatus. Entrance 120 may include one or more sensors (not shown) capable of detecting people, e.g. motion sensors such as laser sensor(s), microwave sensor(s) and/or passive infrared (PIR) sensor(s). The sensor(s) may be coupled to controller 115, which may be configured to transmit an OFF command and/or a 'close casing' command to the disinfection apparatus in the event that the sensor(s) detect entry or attempted entry by a person via entrance 120.

Controller 115 may include an access control mechanism that prevents unauthorised personnel from operating it. For example, controller 115 may include a biometric input mechanism such as an iris scanner and/or fingerprint reader and may be configured to lock the human interface device unless an authorised biometric reading is provided. Other forms of access control, e.g. password or PIN entry, are also possible. As a further example, a physical device that has access credentials stored on it may be required to gain access to controller 115, e.g. a key card such as a Near-Field Communication (NFC) key card, or key fob, and the like.

As space 100 is shown in FIG. 1 is in a calibration mode of the invention, also included within space 100 is a UV sensor 125. Sensor 125 includes an optical detecting component such that sensor 125 is capable of measuring an irradiance of UV light and a wireless communication component that enables sensor 125 to communicate wirelessly with controller 115.

Sensor 125 is portable and relatively compact such that it is capable of being placed in any number of different locations within space 100. In the illustration sensor 125 has been place proximate object 105*b* because the system is shown as being calibrated to disinfect object 105*b*. Once calibration of the system for object 105*b* is complete, sensor 125 can be moved to another location, e.g. proximate object 105*a*, for calibration of the system for disinfecting object 105*a*.

Sensor 125 is wirelessly coupled to controller 115 to enable data gathered by sensor 125 to be transmitted to controller 115. Sensor 125 may transmit raw data to controller 115 for processing, or sensor 125 may itself include a processor and memory such that it performs some processing itself and transmits the results of this processing to controller 115.

Irradiance data collected by sensor 125 is summed over time to determine a UV dose received by sensor 125 over a given time period. As sensor 125 is proximate object 105*b*, it is a safe assumption that object 105*b* has also received a substantially identical UV dose to that measured by sensor 125. The UV dose as measured by sensor 125 can therefore be taken as representative of the dose that the object 105*b* has received and thus it can be reliably determined whether object 105*b* has received a sufficient dose of UV light to provide the required level of disinfection. As is known in the art, disinfection levels may be measured on a logarithmic scale, e.g. 'log 4 disinfection', 'log 5 disinfection' and 'log 6 disinfection'. The present invention is applicable to these and any other level of disinfection.

Sensor 125 is preferably arranged such that the UV light it receives is at least mainly emitted directly by emitter 110, as opposed to reflected from surfaces in space 100. Sensor 125 may be particularly sensitive to specific wavelengths of light that are understood to kill or disable pathogens, e.g. sensor 125 may be a UV-C sensor capable of sensing light in the UV-C wavelength range, particularly 200 nm to 280 nm. Processing may be carried out by sensor 125 and/or controller 115 to determine dose as a function of wavelength. UV light detected by sensor 125 that has a wavelength outside of a wavelength range considered to be effective in killing or disabling pathogens may be disregarded when calculating the dose.

Optionally, sensor 125 may take a background irradiance reading of UV light whilst emitter 110 is switched off. This background UV irradiance may be subtracted from measurements made by sensor 125 whilst emitter 110 is switched on. This can improve the accuracy of the UV dose measurement.

While only one UV sensor is shown in FIG. 1 it will be appreciated that more than one UV sensor can be present in calibration mode. For example, it may be desirable to calibrate the system to disinfect both of objects 105a and 105b simultaneously, in which case two sensors like sensor 125 could be used with one being proximate object 105a and the other being proximate object 105b. Additionally or alternatively, two or more sensors like sensor 125 may be placed proximate a single object if desired, e.g. to take account of shadows that fall on part of the object.

In some cases it may be desirable to define a disinfection program that includes an option to disinfect the space 100 itself. In this case one or more sensors like sensor 125 can be placed within the space, e.g. proximate wall(s) and/or the floor of the space. In this case the object being disinfected is defined as wall(s) and/or floor that the sensor(s) is/are proximate. Distributing sensors around the perimeter of the space 100 allows the entire space to be 'the object' that is being disinfected, such that a program can be stored for disinfection of the entire space.

Referring now to FIG. 2, a method of configuring the disinfecting apparatus described above is provided, according to an embodiment of the invention.

In step 200, an object within the space is selected for disinfection. The selected object may be object 105a and/or object 105b. Here, 'object' is understood to refer to any structure within space 100 including one or more walls and/or the floor. An object selected for disinfection may be defined as a composite of various structures, e.g. the object could be object 105 and object 105b.

In step 205, a UV sensor like sensor 125 is positioned proximate the selected object. For simplicity and ease of description the process is described below with only one sensor present, but it will be appreciated that more than one sensor can be positioned proximate the selected object if desired. This may be advantageous in situations where UV irradiance across the surface of the selected object is expected to vary with position, e.g. where part of the selected object is in shadow.

Optionally, before turning on UV emitter 110, a background UV reading may be taken by the or each sensor 125. If taken, the background reading may be subtracted from the UV dose measured by sensor 125 which may increase the accuracy of the cumulative irradiance measurement.

In step 210, the UV emitter 110 is turned onto cause the emission of UV light within the space. UV emitter 110 may be turned on automatically by controller 115, e.g. via transmission of an 'ON' command by controller 115 to emitter 110. Sensor 125 is preferably positioned so that it at least mainly detects UV light emitted by emitter 110 directly, rather than detecting reflected UV light. Turning the emitter 110 on may involve retracting or opening a UV-opaque casing, if present.

In step 215 the time taken for the sensor 125 to detect a UV dose equal to a threshold dose is measured. This may be achieved by providing a processor and memory within sensor 125, with the processor being configured to sum the measured irradiance over time. Once the measured dose is equal to a threshold dose, the time taken to reach this dose is recorded by sensor 125 and transmitted to controller 115. Alternatively, sensor 125 may transmit raw irradiance measurements to controller 115 in real time or near real time, with controller 115 being configured in that case to calculate a UV dose and compare it with the threshold dose, and record the time when this threshold is reached.

In step 220, emitter 110 is turned off as the threshold UV dose has been reached. Emitter 110 is preferably turned off automatically by controller 115, e.g. by transmission of an 'OFF' command from controller 115 to emitter 110 once the threshold UV dose has been measured by sensor 125. In the case where there are set of sensors deployed, emitter 110 may remain turned on until all of the sensors in the set have recorded a UV dose that is equal to the threshold dose. The time attributed to the disinfection program in this case is preferably equal to the longest time measured by the set of sensors.

In step 225, a disinfection program is created by storing the time taken to reach the threshold dose as measured in step 215 in a memory in associated with an identifier for the selected object. The memory may be a memory of controller 115, for example. The identifier for the selected object preferably includes, or is, a human-readable identifier relating to the selected object, e.g. 'bed', 'walls', 'chair', 'chair and bed', etc. The identifier may also have a machine-readable component, e.g. a unique index value or similar, to ensure that each identifier remains unique. The identifier can be entered via the human interface device of controller 115.

Other information can be included in conjunction with the identifier, including any one or more of: a timestamp indicating a date and time on which the calibration was performed, an operator identifier linked with the operator who performed the calibration, an identifier associated with space 100 (e.g. a room number in a hospital or vehicle registration plate number of an ambulance), a unique identifier corresponding to sensor 125 such as a MAC address, and the like.

It is also contemplated that multiple programs can be defined for the same object, each program specifying a different disinfection level. Object 105a, for example, may have two programs defined: a standard disinfection and a deep disinfection, the former of which disinfects to the log 4 level and the latter to the log 6 level. It will be appreciated in this case that the calibration process of FIG. 2 would be performed for each disinfection level separately.

It is further contemplated that multiple programs can be defined for the same object, each program specifying a different location of the object within space 100. This may be useful in situations where the object has several predefined locations that it is switched between depending on the configuration of space 100. For example, a hospital room may have a one bed configuration and a two bed configuration, with the invention enabling separate programs to be stored for each configuration if desired. It will be appreciated in this case that the calibration process of FIG. 2 would be performed for each configuration separately.

Controller 115 is preferably configured to interrupt the process of FIG. 2 immediately should it detect a person attempting to enter space 100, e.g. via motion sensor(s) proximate door 120. In such a case the calibration process for the currently selected object may be paused and continued once the person has left space 100, or cancelled and restarted from the beginning.

Following step 225, it is decided whether calibration is complete for all objects in space 100. In the case that there are more objects to calibrate the system for, the process returns to step 200 and the operator selects another object and repositions sensor 125 accordingly.

In the case where there are no more objects to perform calibration for, the operator can signal this to controller 115 by selecting an 'end calibration' option in step 230. Sensor 125 can also be removed from space 100.

At the end of a calibration process, the memory of controller 115 may store a table similar to Table 1 below.

TABLE 1

| Time (s) | Identifier |
| --- | --- |
| 300 | Chair |
| 600 | Bed and chair |
| 1800 | Room |

Here, three programs have been configured according to the calibration process of FIG. 2. A first program is for disinfecting a bed and lasts 300 seconds. A second program is for disinfecting a bed and chair and lasts 600 seconds. A third program is for disinfecting a room and lasts for 1800 seconds. Table 1 is purely exemplary to illustrate the operation of the invention and is in no way limiting in scope.

Figure 3:
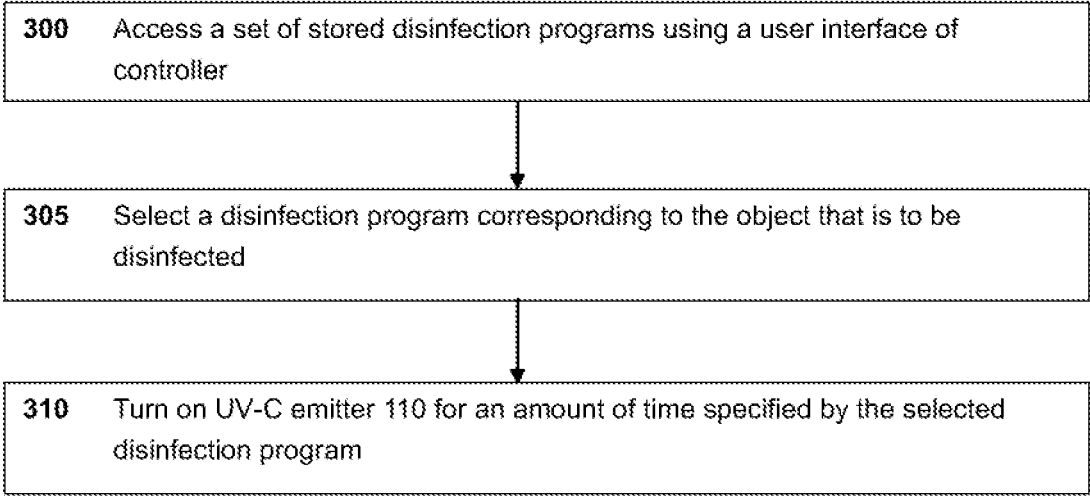
FIG. 3 illustrates a method of performing a disinfection cycle for a desired object according to an embodiment of the invention

Referring to FIG. 3, an operator can perform a disinfection cycle for a desired object as follows.

In step 300, the operator accesses a set of stored disinfection programs using a user interface of controller 115. The user interface may replicate the information shown in Table 1, for example—e.g. a list of identifiers corresponding to objects in space 100 may be displayed on a touchscreen with an indication of the disinfection time next to each identifier. This is only one exemplary format and the skilled person will appreciate that substantial variation in the design of this user interface is possible. All such variants are within the scope of the present invention.

The operator may be required to provide an authentication credential, e.g. a biometric reading, password, PIN, or a credential stored on a key card, key fob, etc., to gain access to the user interface displaying the set of stored disinfection programs. Access control of this type prevents unauthorised persons from initiating a disinfection cycle.

In step 305, a disinfection program corresponding to the object that is to be disinfected is selected. The selection can be made using the human interface device of controller 115, e.g. tapping the identifier corresponding to the object on a touchscreen of controller 115.

In step 310, emitter 110 is turned on for an amount of time specified by the disinfection program selected in step 305. This process can be entirely automatic—controller 115 can transmit an 'ON' command to emitter 110 concurrently with starting a timer (e.g. a system clock).

Controller 115 can wait until the timer has measured the amount of time specified by the disinfection program and then transmit an 'OFF' command to emitter 110.

Advantageously the operator can be confident that the selected disinfection program will disinfect the selected object to the required level because the calibration process of FIG. 2 has demonstrated that this is the case. However, it is not necessary for sensor 115 to be placed in space 100 each time the disinfection program is to be performed because the parameters for the program are stored by controller 115. This has an associated time saving and reduction in complexity of the disinfection process without compromising efficacy at all. This may also advantageously mean that calibration can be performed by a more highly trained operator whereas a disinfection program can be initiated by an operator that is not so highly trained. Additionally, since a particular object can be selected via the disinfection program, emitter 110 generates UV light only for the time required to disinfect the object. This tends to lead to lower total exposure of the space to UV light, with a corresponding reduction in the degradation of materials in the space owing to their exposure to UV light compared with a disinfection process that is not object-specific. Furthermore, the total time that the space is out of action owing to disinfection is reduced compared with a disinfection process that is not object-specific.

Preferably a safety check is performed before emitter 110 is turned on to determine whether or not any people are within space 100. If any people are detected, e.g. using one more motion sensors within space 100, controller 115 may prevent the disinfection program from being initiated. An error or warning message may be displayed on a display of the controller 115 informing the operator that disinfection cannot begin owing to the fact that space 100 is occupied.

Most UV light sources are subject to some degradation over their operational lifetime as components become worn. The UV irradiance of emitter 110 can therefore vary over time, typically decreasing with the age of emitter 110. For this reason the calibration process of FIG. 2 can be repeated for a given object over a suitable timescale, e.g. every 3 or 6 months, to ensure that such degradation is captured and taken account of. Controller 115 may flag a disinfection program that is due for a repeat calibration to the operator, e.g. via a visual indicator on a user interface of the controller. Controller 115 may present this flag based on a number of disinfection cycles that have been performed and/or a time that has elapsed since the most recent calibration was performed. Controller 115 may be configured to disable a disinfection program that requires recalibration, e.g. by marking it as 'expired' or equivalent.

Preferably in this case the flag appears some time before the disinfection program needs to be recalibrated to provide sufficient time for recalibration to be organised before expiry of the disinfection program. In this way the invention can ensure that disinfection efficacy is maintained over the entire operational lifetime of the disinfection apparatus.

Figure 4:
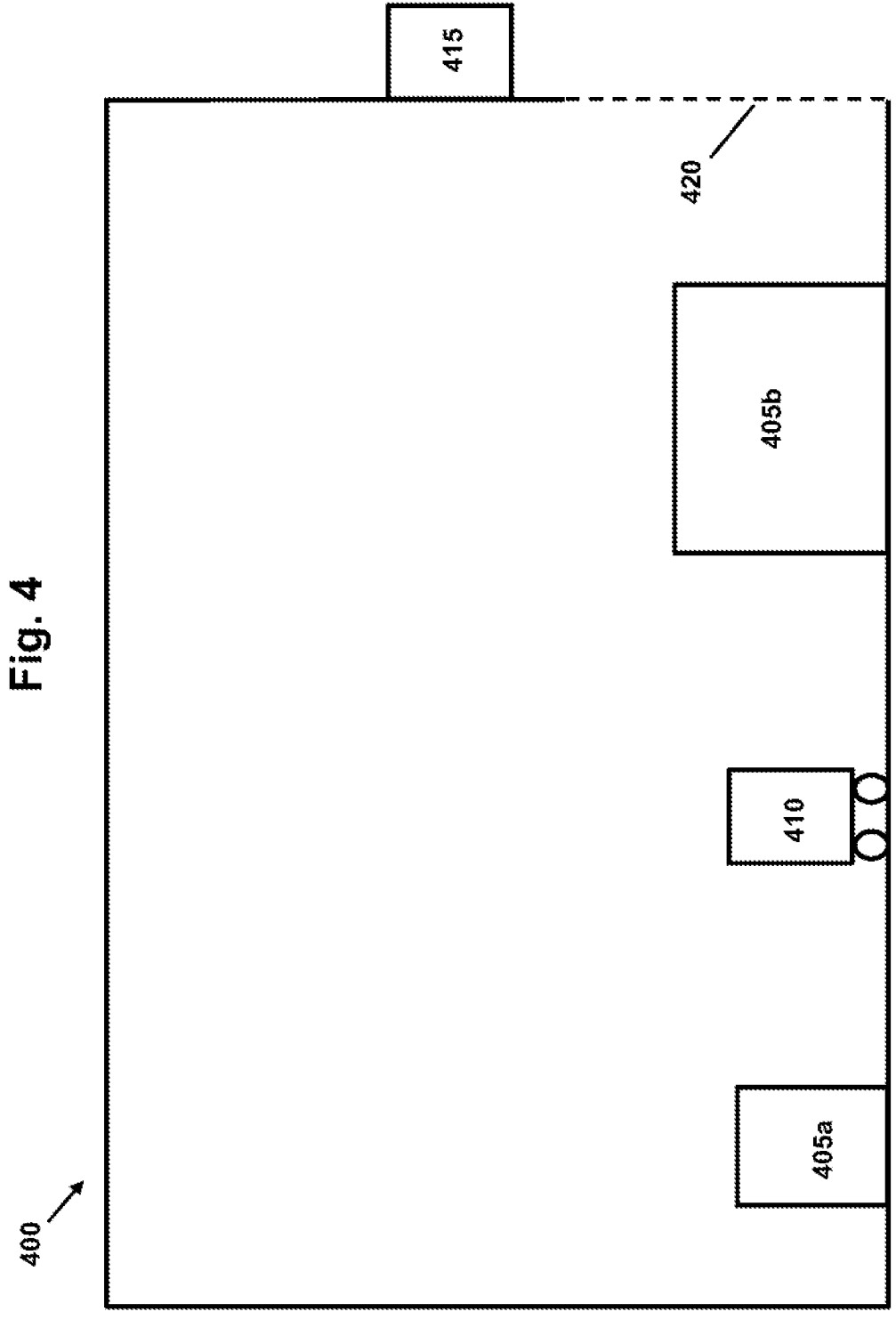
FIG. 4 is a schematic drawing of an arrangement suitable for implementing a pathogen-specific operating mode according to an embodiment of the invention.

FIG. 4 shows an arrangement suitable for implementing a pathogen-specific operation mode of the present invention. The elements of FIG. 4 are identical to their corresponding elements shown in FIG. 1 other than as set out below. A space 400 containing objects 405a, 405b to be disinfected is shown in schematic form. In the interests of brevity, elements that are identical in both figures are not described again here; instead, reference is made to the earlier description in connection with FIG. 1.

Emitter 410 differs from emitter 110 in that emitter 410 does not have to be a fixed emitter, but instead can be a mobile UV emitter as illustrated. It should be clear, however, that emitter 410 could be a fixed emitter—either a fixed or mobile emitter is usable with the embodiment of FIG. 4. Emitter 410 does not have to be a single unit, and multiple fixed or mobile emitters can be provided in space 400. A combination of fixed and mobile emitters may also be used. Mobile emitters per se are known and any such currently known or future developed mobile emitter can be used with the invention.

Controller 415 is the same as controller 115 in that it includes a processor, memory and human interface device. In the illustrated embodiment, the controller 415 is wall mounted and located outside of space 400 next to an entrance 420 to space 400. Controller 415 is also configured to send control signals to the disinfection apparatus in the same manner as controller 115, and may be a fixed or mobile controller as in the case of controller 115.

Additionally, the memory of controller 415 stores a data structure that includes at least an identification of a particular pathogenic organism and an associated disinfection time. Preferably, the data structure also includes a set of disinfection times, each corresponding to a particular disinfection level (e.g. 'log 4', 'log 5', 'log 6'). An exemplary form for the data structure stored in the memory of controller 415 is shown below in Table 2.

TABLE 2

| Pathogenic organism | Disinfection level | Disinfection cycle time (s) |
|---|---|---|
| Clostridium difficile | Log 4 | 300 |
| Clostridium difficile | Log 5 | 500 |
| Clostridium difficile | Log 6 | 750 |
| COVID-19 | Log 4 | 600 |
| COVID-19 | Log 5 | 900 |
| COVID-19 | Log 6 | 1200 |

The disinfection times shown in Table 2 are purely exemplary and should not be taken as actual values for disinfection of a space containing the listed pathogens. In practice the disinfection cycle time will be determined through experimentation, e.g. exposing a test surface with a known population of a target pathogenic organism present on it to UV light and observing the kill or disable proportion as a function of time.

A user interface of controller 415 may enable an operator to select, via the human interface device, one or more target organisms. A required disinfection level may optionally also be specified. Controller 415 may be configured to select an appropriate duration for a disinfection cycle based on the selection(s) provided by the operator. The duration of the disinfection cycle may be selected as the longest disinfection cycle time in a set of selected target organisms. For example, referring to Table 2, if the operator selected '*Clostridium difficile*' with a log 6 disinfection level and 'COVID-19' with a log 4 disinfection level, controller 415 would set the disinfection cycle time to 750 seconds, this being the longer of 600 and 750 seconds.

The user interface of controller 415 may provide some mechanism by which the operator can indicate that selection of all target pathogenic organisms is complete. This may comprise, for example, an 'ok', 'proceed' or 'done' button, or equivalent graphical user interface element. Once the operator has indicated that selection of all target pathogenic organisms is complete, controller 415 can initiate a disinfection cycle having a duration selected as discussed in the immediately preceding paragraph.

It will be appreciated that in the case where emitter 410 is a fixed emitter, the embodiment of FIG. 4 can be combined with the embodiment of FIG. 1. That is, the invention encompasses embodiments in which both object selection and pathogenic organism selection is possible. Such embodiments are particularly efficient as the disinfection cycle has a duration that is tailored for both the object(s) being disinfected and the pathogenic organisms(s) that are present on a surface of the selected object(s). Degradation of materials within the space being disinfected owing to exposure to UV light, and downtime of the space, is thus advantageously kept to a minimum without compromising disinfection efficacy.

Functionality may be provided by controller 415 to enable the operator to save a particular selection of target pathogenic organisms, e.g. as an entry in a 'frequency used disinfection programs' list, or the like. The operator may be able to specify a user-friendly name for the saved selection, e.g. 'C. Diff & COVID-19' in the example above. Subsequent to this, the operator can select the saved selection rather than having to select each individual pathogenic organism repeatedly. Controller 415 may additionally or alternatively be configured to automatically add entries to the frequency used disinfection programs list and/or to provide a 'last N' program list, N being an integer greater than or equal to 1, which stores the last N disinfection programs that were run.

The pathogen-specific operation mode may be particularly useful in circumstances where it is known or strongly suspected that the majority pathogenic organism in a space is a particular organism or set of organisms—for example, in the case where a hospital room has been occupied by a patient having a particular infection or set of infections.

Referring now to FIG. 5, an operator can perform a disinfection cycle for target pathogenic organism(s) as follows.

In step 500, a set of available target pathogenic organisms is presented using a user interface of controller 415. This presentation can take any format that conveniently enables the operator to select entries corresponding to particular pathogenic organisms, e.g. a list based upon the information set out in Table 2 above.

In step 505, controller 415 receives a selection of one or more target pathogenic organisms, e.g. input from an operator provided by interacting with a touchscreen, clicking a mouse or pressing a key on a keyboard.

In step 510, controller 415 determines a longest time associated with the selected one or more target pathogenic organisms. This may be implemented by machine-readable code that compares the time associated with each entry and determines the largest value.

In step 515, controller 415 initiates a disinfection cycle having a duration equal to the longest time by turning on emitter 415 for an amount of time equal to the longest time such that reliable, efficient and effective disinfection of the space in respect of the target pathogenic organism(s) is achieved.

Many modifications and variations to the specifics of the invention will be apparent to a person skilled in the art having the benefit of the present disclosure. All such modifications and variations are also embodiments of the invention.

What is claimed is:

1. A method for configuring a disinfection apparatus, the disinfection apparatus secured to a fixed surface within a room or an interior of a vehicle, the disinfection apparatus comprising a UV emitter, the method comprising:

a) selecting a first object within the room or vehicle interior for disinfection;

b) positioning a first UV sensor proximate the first object;

c) measuring a background UV irradiance by using the UV sensor;

d) operating a controller communicably coupled to the UV emitter and the first UV sensor, the controller comprising a processor operable to respond to computer-readable instructions stored in memory, by:

(i) turning the UV emitter on to cause an emission of UV light within the room or vehicle interior;

(ii) measuring a time that is taken for the first UV sensor to detect a UV dose equal to a threshold dose, wherein the background UV radiance is subtracted from the UV dose;

(iii) automatically turning off the UV emitter when the threshold dose is reached;

(iv) creating a first disinfection program by storing the time taken in a memory in association with an identifier for the first object;

e) repeating steps (a) to (d) to create a second disinfection program corresponding to a second object within the room or vehicle interior;

f) completing the configuration by removing the first UV sensor from the room or vehicle interior;

g) selecting the first disinfection program or the second disinfection program; and h) responsive to the selecting, automatically turning on the UV emitter for an amount of time specified by the selected disinfection program.

2. The method of claim 1, wherein the controller is located remotely from the UV emitter, and step d) (iv) includes transmitting the time taken to the controller.

3. The method of claim 1 or claim 2, wherein step b) comprises arranging a plurality of UV sensors proximate the first object, the first UV sensor being one of the plurality of UV sensors;

wherein step d) (ii) further comprises:

measuring a respective plurality of times taken for each of the plurality of UV sensors to measure a cumulative UV irradiance equal to the threshold value;

calculating a longest time of the plurality of times;

and wherein step d) (iv) comprises storing the longest time in the memory.

4. The method of claim 3, wherein the method further comprises, subtracting the background irradiance from the cumulative UV irradiance.

5. The method of claim 1 or 2, wherein the first object comprises a wall and/or floor of the room or vehicle interior.

6. A method for disinfecting an object in a room or vehicle interior using a disinfection apparatus secured to a fixed surface within the room or vehicle interior and comprising a UV emitter, the method comprising:

configuring the disinfection apparatus by:

a) selecting a first object within the room or vehicle interior for disinfection;

b) arranging a first UV sensor proximate the first object;

c) measuring a background UV irradiance by using the first UV sensor;

d) operating a controller communicably coupled to the UV emitter and the first UV sensor, the controller comprising a processor operable to respond to computer-readable instructions stored in memory, by:

(i) turning the UV emitter on to cause an emission of UV light within the room or vehicle interior;

(ii) measuring a time that is taken for the first UV sensor to detect a UV dose equal to a threshold dose, wherein the background UV radiance is subtracted from the UV dose;

(iii) automatically turning off the UV emitter when the threshold dose is reached;

(iv) creating a first disinfection program by storing the time taken in a memory in association with an identifier for the first object;

e) repeating steps (a) to (d) to create a second disinfection program corresponding to a second object within the room or vehicle interior;

f) completing the configuration by removing the first UV sensor from the room or vehicle interior; and g) initiating a decontamination cycle to disinfect at least the first object in the room or vehicle interior by:

i) selecting either the first of the second disinfection program using a user interface of the controller coupled to the disinfection apparatus and to the memory; and ii) responsive to the selecting, automatically turning the UV emitter on for an amount of time specified by the disinfection program.

7. A system for disinfecting a room or vehicle interior, the system comprising:

a UV emitter secured to a fixed surface within the room or vehicle interior;

a controller located remotely from the UV emitter; and a UV sensor configured to measure a background UV irradiance;

wherein the controller comprises a processor and a memory, the memory storing computer-readable instructions that, when executed, cause the processor to:

transmit a control signal to the UV emitter to cause the UV emitter to turn on;

determine a time taken for the UV sensor to measure a UV dose equal to a threshold dose wherein the background UV radiance is subtracted from the UV dose;

automatically turn off the UV emitter when the threshold dose is reached; and create a first disinfection program by storing the time taken in the memory in association with an identifier for a first object located proximate the UV sensor based on the time taken for the first UV sensor to detect a UV dose equal to a threshold dose, the disinfection program operable to disinfect the room or vehicle interior;

create a second disinfection program by storing the time taken in the memory in association with an identifier for a second object located proximate the UV sensor based on the time taken for the first UV sensor to detect a UV dose equal to a threshold dose, the disinfection program operable to disinfect the room or vehicle interior;

wherein the computer-readable instructions further cause the processor to:

receive a selection of either the first or the second disinfection program via a user interface of the controller; and transmit a control signal to the UV emitter to cause the UV emitter to turn on for a time equal to the time taken as stored in the memory.

* * * * *